United States Patent
Tsai et al.

(10) Patent No.: US 9,063,091 B2
(45) Date of Patent: Jun. 23, 2015

(54) TEST STRIPS AND METHOD FOR READING TEST STRIPS

(71) Applicant: iXensor Inc., Grand Cayman (KY)

(72) Inventors: Tungmeng Tsai, Taipei (TW); Chieh Hsiao Chen, Taipei (TW); Yenyu Chen, Taipei (TW)

(73) Assignee: IXENSOR INC. (KY)

(*) Notice: Subject to any disclaimer, the term of this patent is extended or adjusted under 35 U.S.C. 154(b) by 0 days.

(21) Appl. No.: 13/798,175

(22) Filed: Mar. 13, 2013

(65) Prior Publication Data

US 2013/0267032 A1    Oct. 10, 2013

Related U.S. Application Data

(60) Provisional application No. 61/621,007, filed on Apr. 6, 2012, provisional application No. 61/621,004, filed on Apr. 6, 2012, provisional application No. 61/749,811, filed on Jan. 7, 2013.

(51) Int. Cl.
| | |
|---|---|
| *G01N 21/78* | (2006.01) |
| *G01N 21/77* | (2006.01) |
| *G01N 21/75* | (2006.01) |
| *G01N 21/84* | (2006.01) |

(52) U.S. Cl.
CPC ....... *G01N 21/78* (2013.01); *Y10T 436/144444* (2015.01); *G01N 21/8483* (2013.01)

(58) Field of Classification Search
CPC ....... G01N 21/78; G01N 21/77; G01N 21/75; G01N 21/00; G01N 21/8483; Y10T 436/14; Y10T 14/144444

USPC ............ 436/95, 94, 93, 91, 164; 422/400, 50
See application file for complete search history.

(56) References Cited

U.S. PATENT DOCUMENTS

| | | | |
|---|---|---|---|
| 5,077,010 A | 12/1991 | Ishizaka et al. | |
| 5,277,870 A * | 1/1994 | Fuller et al. | 422/82.05 |
| 5,281,395 A | 1/1994 | Markart et al. | |
| 5,556,761 A | 9/1996 | Phillips | |
| 5,719,034 A * | 2/1998 | Kiser et al. | 435/14 |
| 5,843,691 A | 12/1998 | Douglas et al. | |
| 6,168,957 B1 | 1/2001 | Matzinger et al. | |
| 6,531,322 B1 | 3/2003 | Jurik et al. | |
| 6,572,822 B2 | 6/2003 | Jurik et al. | |

(Continued)

FOREIGN PATENT DOCUMENTS

WO    WO 2005/088519    *    9/2005    ............... G06K 9/00

OTHER PUBLICATIONS

Nicola Dell et al., "Towards a Point-of-Care Diagnostic System: Automated Analysis of Immunoassay Test Data on a Cell Phone", Jun. 28, 2011, NSDR'11, Bethesda, Maryland, USA.

*Primary Examiner* — Christine T Mui
(74) *Attorney, Agent, or Firm* — SU IP Consulting

(57) ABSTRACT

A specimen test strip is provided to detect a characteristic of an analyte in a specimen sample. The specimen test strip includes a reaction area to receive the specimen sample and a color calibration area to determine a color, or a color and a color intensity, of the reaction area after receiving the specimen sample. The specimen test strip may further include a temperature indication area to correct a measurement of the characteristic of analyte.

15 Claims, 19 Drawing Sheets

(56) References Cited

U.S. PATENT DOCUMENTS

| | | |
|---|---|---|
| 7,988,845 B2 | 8/2011 | Heller et al. |
| 2006/0024835 A1* | 2/2006 | Matzinger et al. .............. 436/95 |
| 2007/0279328 A1 | 12/2007 | Takada et al. |
| 2009/0098657 A1* | 4/2009 | Blais et al. .................... 436/147 |
| 2010/0216175 A1* | 8/2010 | Melker et al. ................... 435/14 |
| 2012/0045842 A1* | 2/2012 | Petrich et al. ................... 436/95 |
| 2012/0089051 A1 | 4/2012 | Draudt et al. |
| 2012/0201755 A1* | 8/2012 | Rozakis et al. ................ 424/9.1 |

* cited by examiner

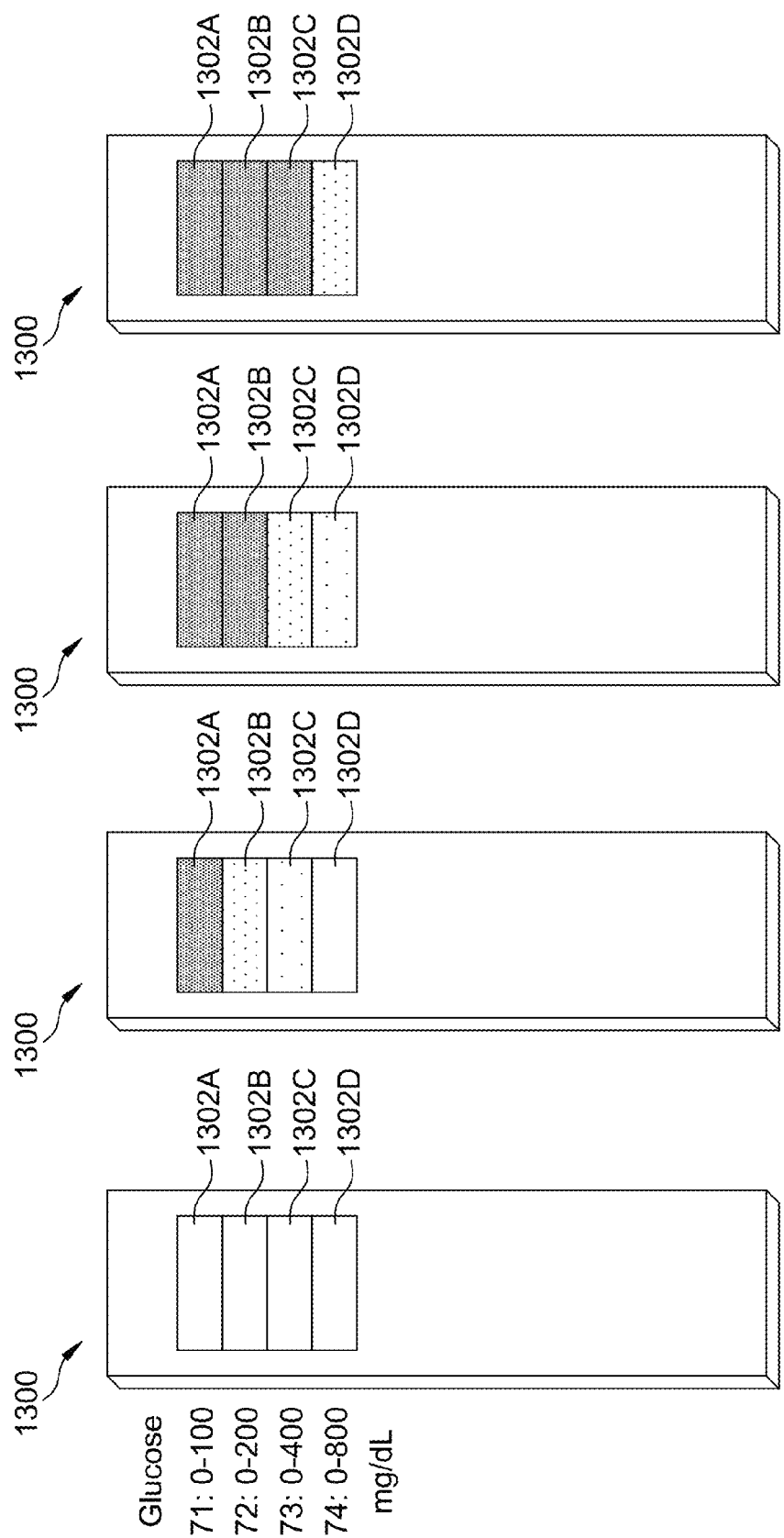

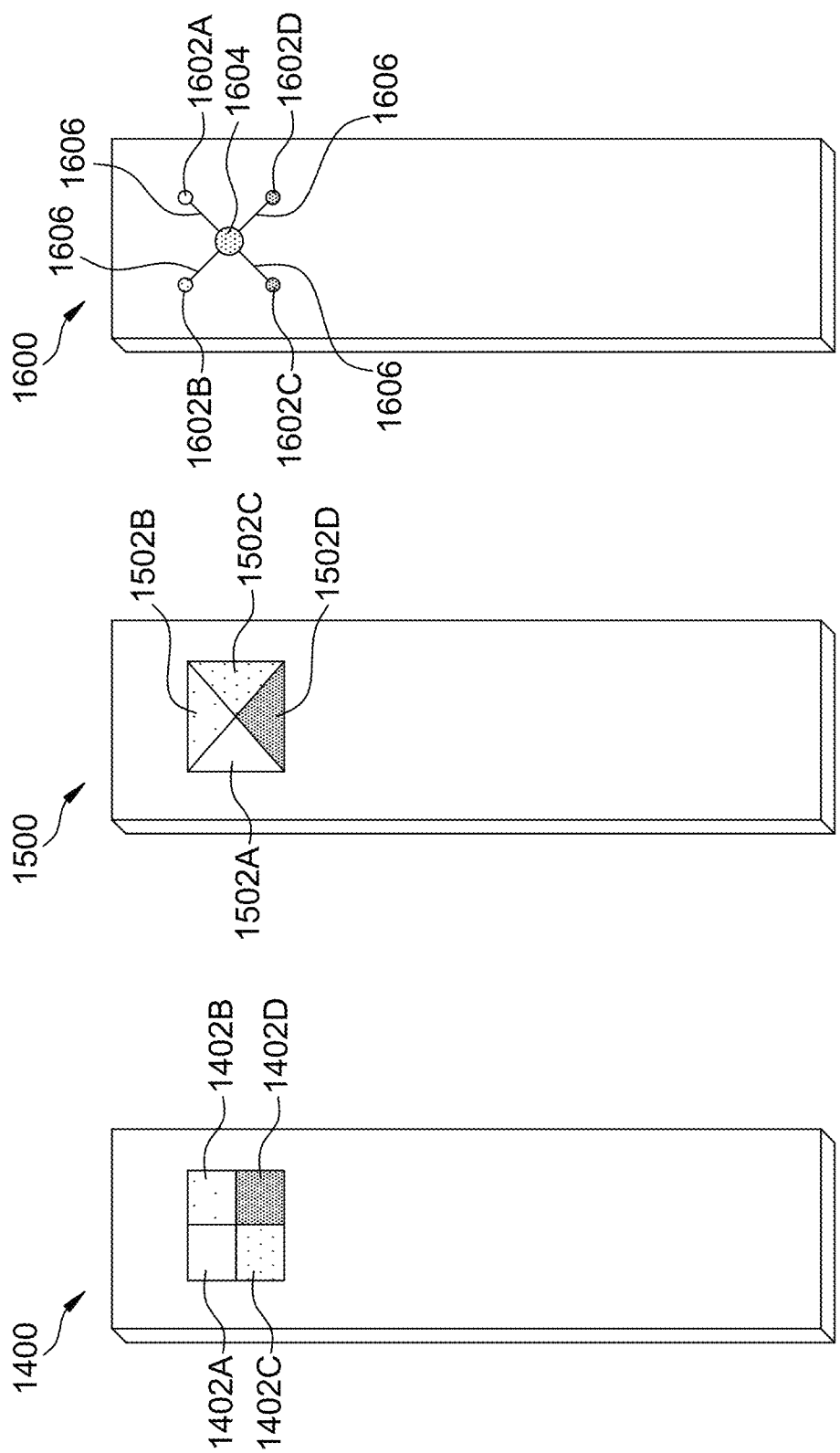

TEST STRIPS AND METHOD FOR READING TEST STRIPS

CROSS-REFERENCE TO RELATED APPLICATIONS

This application claims the benefit of U.S. Provisional Application No. 61/621,004, filed Apr. 6, 2012, U.S. Provisional Application No. 61/621,007, filed Apr. 6, 2012, and U.S. Provisional Application No. 61/749,811, filed on Jan. 7, 2013.

INCORPORATION BY REFERENCE

All publications and patent applications mentioned in this specification are herein incorporated by reference to the same extent as if each individual publication or patent application was specifically and individually indicated to be incorporated by reference. For example, this application incorporates by reference in their entireties U.S. Provisional Application No. 61/621,004, filed Apr. 6, 2012, U.S. Provisional Application No. 61/621,007, filed Apr. 6, 2012, and U.S. Provisional Application No. 61/749,811, filed on Jan. 7, 2013.

FIELD

The present disclosure generally relates to photometric analysis of one or more analytes applied to a test strip.

BACKGROUND

FIG. 1 shows a prior art specimen test strip 100 with a reaction area 102. Reaction area 102 contains reagents that react with an analyte in a specimen sample, such as glucose in a blood sample. When the specimen sample reaches reaction area 102, reaction area 102 changes color according to a characteristic of the analyte, such as the glucose level in blood. The user visually compares the color of reaction area 102 against a chart 104 to correlate the color of reaction area 102 to the characteristic of the analyte. Alternatively the user inserts specimen test strip 100 into a meter, which optically determines the characteristic of the analyte.

SUMMARY

According to aspects of the present disclosure, a specimen test strip to detect a characteristic of an analyte in a specimen sample is provided with a reaction area configured to receive the specimen sample, and a color calibration area configured to determine a color of the reaction area after receiving the specimen sample. In some embodiments, a plurality of reaction areas are provided, each configured to detect a different range of values of the characteristic of the analyte.

According to other aspects of the present disclosure, methods for a computing device with an imaging device to read a specimen test strip to detect a characteristic of an analyte in a specimen sample are provided. In some embodiments, the method comprises capturing one or more images of the specimen test strip, wherein each image includes a reaction area and a color calibration area on the specimen test strip. In these embodiments, the method further comprises determining a color of the reaction area based on the color calibration area from the one or more images, and correlating the color of the reaction area to a value of the characteristic of the analyte.

In some embodiments, a method is provided which comprises capturing at least two images of the specimen test strip, wherein each image includes a reaction area. The method further comprises determining a color intensity change of the reaction area from the images, and determining a time difference between when the images were captured. The method also comprises correlating the color intensity change and the time difference to a value of the characteristic of the analyte.

In some embodiments, a method is provided which comprises capturing a first image of the specimen test strip. The image includes reaction areas, each configured to detect a different range of values of a characteristic of an analyte. The method further comprises selecting one of the reactions areas and correlating the selected reaction area to a value of the characteristic of the analyte.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are therefore not to be considered limiting of its scope, the disclosure will be described with additional specificity and detail through use of the accompanying drawings.

In the drawings:

FIG. 13A shows a specimen test strip that includes a set of reaction areas to detect different ranges of values of an analyte characteristic in a specimen sample in one or more examples of the present disclosure;

FIGS. 13B, 13C, and 13D show the specimen test strip of FIG. 13A after receiving specimen samples having different values of an analyte characteristic in one or more examples of the present disclosure;

FIG. 14 shows a specimen test strip that includes a set of reaction areas to detect different ranges of values of an analyte characteristic in a specimen sample in one or more examples of the present disclosure;

FIG. 15 shows a specimen test strip that includes a set of reaction areas to detect different ranges of values of an analyte characteristic in a specimen sample in one or more examples of the present disclosure;

FIG. 16 shows a specimen test strip that includes a set of reaction areas to detect different ranges of values of an analyte characteristic in a specimen sample in one or more examples of the present disclosure;

DETAILED DESCRIPTION

Figure 1:
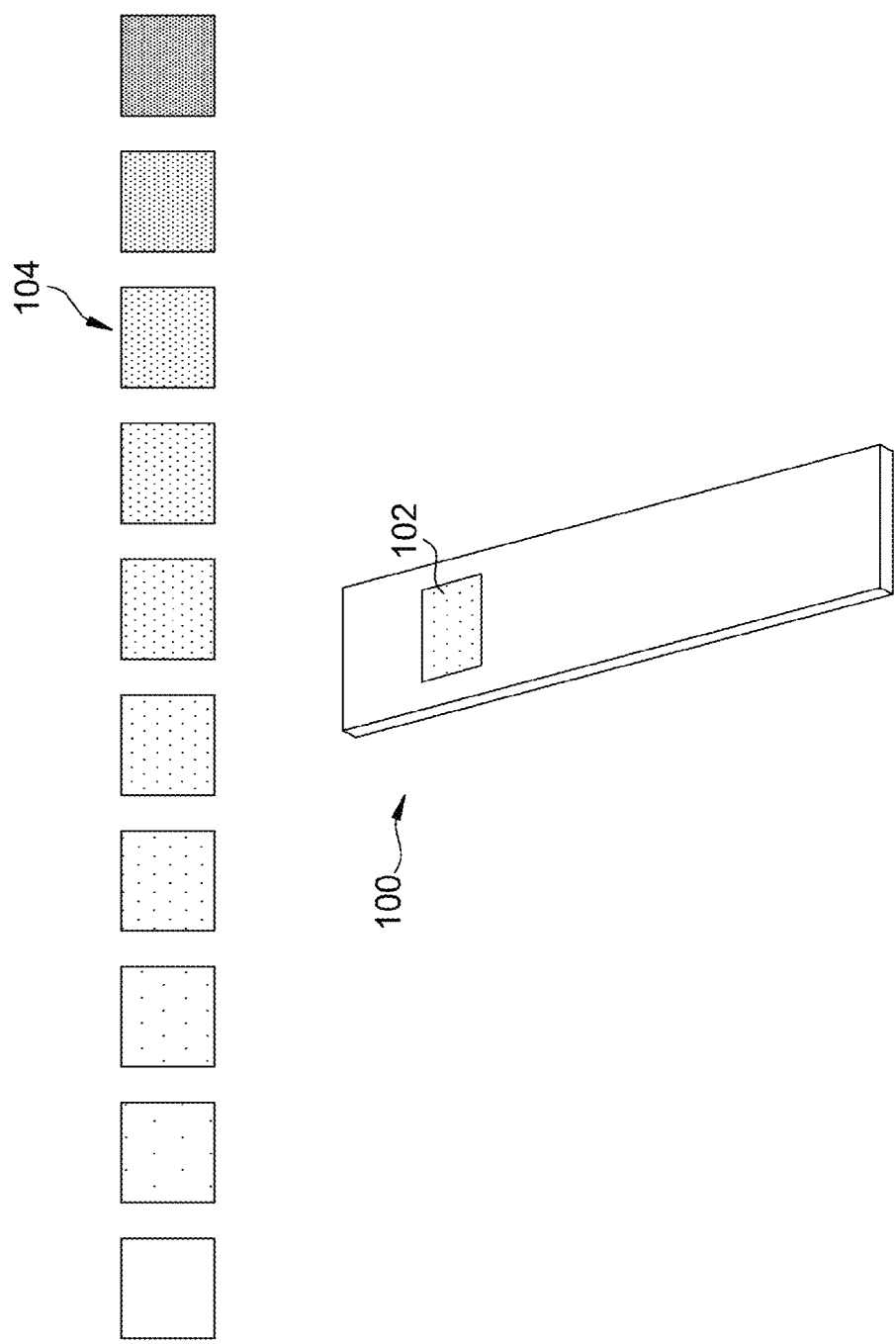
FIG. 1 shows a prior art specimen test strip.
Figure 2:
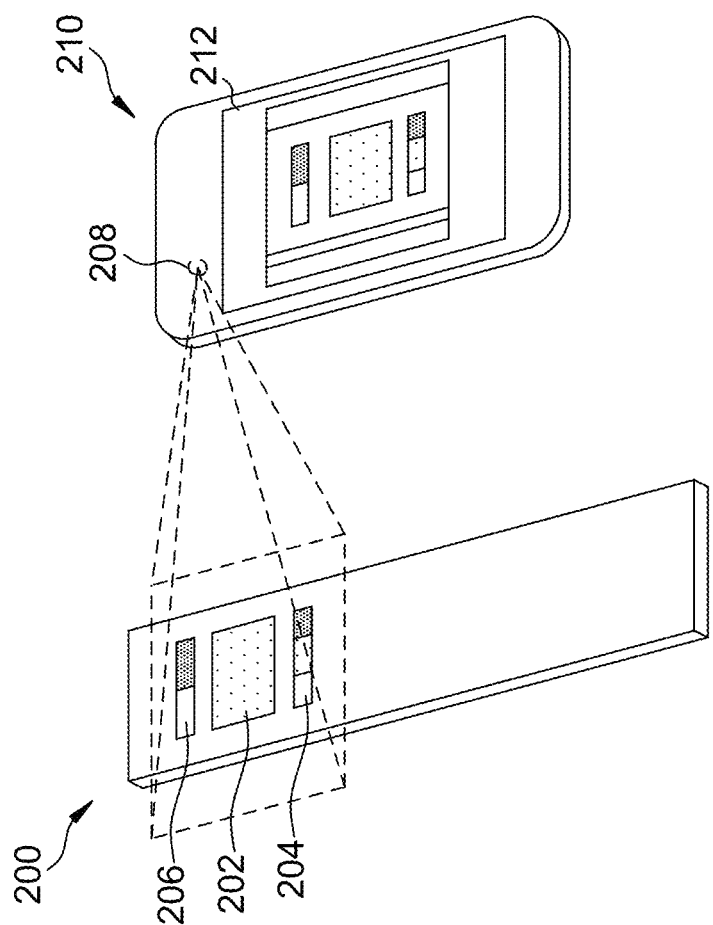
FIG. 2 shows a specimen test strip with a reaction area, a color calibration area, and a temperature calibration area in one or more examples of the present disclosure.

FIG. 2 shows an exemplary embodiment of a specimen test strip 200 in one or more examples of the present disclosure. Specimen test strip 200 includes a reaction area 202 to receive a specimen sample. Reaction area 202 includes reagents to chemically react with the analyte in the specimen sample and produce one or more color parameters that are proportional to the value of a characteristic of the analyte in the specimen sample. In some embodiments, the one or more color parameters includes the color or both the color and the color intensity of reaction area 202. In one example, the color is the hue of reaction area 202 and the color intensity is the lightness of reaction area 202. The hue and the lightness are color components in the hue, saturation, and lightness (HSL) color space, which are determined from the red, green, and blue (RGB) values of pixels captured by a camera. For convenience, color and color intensity may be collectively referred to as color. The reagents may be analyte specific and may include one or more enzymes, one or more antibodies, and/or one or more dyes. For example, reagents for testing glucose in blood may include glucose oxidase, heteropoly acid, and tetradecyl ammonium nitrate.

In one example, specimen test strip 200 includes a color calibration area 204 that is part of specimen test strip 200. In one example, color calibration area 204 is used to determine the color of reaction area 202 under different lighting conditions. In such an example, color calibration area 204 may be a color chart having an arrangement of known color samples. In another example, color calibration area 204 is used to correct the detected color of reaction area 202 to remove the effects of the light condition. In such an example, color calibration area 204 may be a gray card of known reflectance (e.g., 18%) that serves as a white balance reference for color correction. Gray card 204 may also serve as an exposure reference when a computing device 210 captures an image 212 of specimen test strip 200. In one example, color chart or gray card 204 is printed on specimen test strip 200.

In one example, color calibration area 204 is a dummy reaction area having one or more known colors. In use, dummy reaction area 204 remains the same color or colors because it is devoid of one or more enzymes, one or more antibodies, or one or more dyes. In another example, dummy reaction area 204 remains the same color or colors because it does not receive any specimen sample.

In one example, specimen test strip 200 includes a temperature calibration area 206 that is part of specimen test strip 200 along with reaction area 202 and color calibration area 204. Temperature calibration area 206 changes color according to its temperature and it is used to correct the color of reaction area 202 as the chemical reaction between the reagents and the analyte may be affected by the temperature of specimen test strip 200. In one example, temperature calibration area 206 includes an organic material such as a thermochromic dye (e.g., leuco dyes such as spirolactones, fluorans, spiropyrans, or fulgides), an inorganic material such as titanium dioxide, zinc oxide, or indium oxide, or a thermochromic liquid crystal. In another example, temperature calibration area 206 is a chip, a mechanical device, or an electromechanical device that indicates a temperature. Instead of or in addition to using temperature calibration area 206, computing device 210 may use a built-in temperature sensor to approximate or determine the temperature of reaction area 202.

Using an imaging device 208 on computing device 210, a user captures an image 212 of reaction area 202 and at least one of color calibration area 204 and temperature calibration area 206. Imaging device 208 may be a camera, a scanner, or another similar device, and computing device 210 may be a smart phone, a tablet computer, a laptop computer, a desktop computer, or another similar device. Computing device 210 runs a diagnostic application that analyzes image 212 to determine the analyte characteristic from the color of reaction zone 202.

In one example, the diagnostic application determines the color of reaction area 202 using color calibration area 204 in image 212. When color calibration area 204 is a color chart, the diagnostic application matches the color of the entire or part of reaction area 202 to one of the known color samples of color calibration area 204 to determine the color of reaction area 202. Alternatively the diagnostic application may manipulate image 212 until color chart 204 matches its known colors and then reads all or part of the color of reaction area 202. When color calibration area 204 is a gray card, the diagnostic application manipulates image 212 until gray card 204 in image 212 has the proper white balance and then reads the color of reaction area 202.

In another example, the diagnostic application determines the color of reaction area 202 using color calibration area 204 in image 212 and corrects the color using temperature calibration area 206 in image 212. The diagnostic application determines the temperature of specimen test strip 200 from temperature calibration area 206 or a built-in temperature sensor in computing device 210, and then corrects the color of reaction area 202 for the temperature using a known relationship between temperature and color for reaction area 202. This relationship may be determined experimentally, mathematically, or both. The diagnostic application may perform the color correction using temperature calibration area 206 before or after any of the other corrections described in the present disclosure.

In one example, the diagnostic application calibrates the illumination of image 212 before using color calibration area 204 and temperature calibration area 206. The diagnostic application estimates an illumination profile of reaction area 202 to determine if the illumination is uniform. The diagnostic application determines the illumination profile from RGB values of at least two locations that span reaction area 202 or color calibration area 204 (e.g., opposing corner pixels 506 and 508 in FIG. 5). When the illumination profile between the two locations is greater than the noise level by a threshold amount (e.g., the illumination profile is twice the noise level), the illumination on reaction area 202 is not uniform and the diagnostic application corrects the illumination of image 212. In one example, the diagnostic application uses the following formula to correct the illumination of image 212:

$$RGB_{new} = i*(R(x,y),G(x,y),B(x,y))/(R_{est}(x,y),G_{est}(x,y),B_{est}(x,y))$$

where $R(x,y)$, $G(x,y)$, $B(x,y)$ are the original RGB values of a pixel, $R_{est}(x,y)$, $G_{est}(x,y)$, $B_{est}(x,y)$ are the estimated RGB values of the illumination profile at the same pixel, and i is the maximum RGB values for the color of the reaction area. For example, color calibration area 204 may include a white ring around reaction area 102. Assume in image 212 the RGB values of corner 506 are (200,200,200) and that of corner 508 are (100,100,100). Further assume that the illumination profile is linear. Based on these assumptions, a white point at a central pixel 510 of reaction area 502 in FIG. 5 would have RGB values of (150,150,150). When the color at pixel 510 is not white, say it instead has RGB values of (125,75,75), the new RGB values for the central point are i*(125,75,75)/(150, 150,150), where i is (255,255,255).

After the one or more calibrations described in the present disclosure, the diagnostic application samples pixels from reaction area 202 (e.g., 50 to 100 pixels) and determines their values for the one or more color parameters (e.g., the color or the color and the color intensity). The diagnostic application averages the values for the one or more color parameters and correlates the one or more averaged color parameters to the value of the analyte characteristic (e.g., the concentration level of glucose in blood).

In one example, reaction area 202, color calibration area 204, and temperature calibration area 206 are rectangular, and areas 204 and 206 are located adjacent to the top and bottom sides of area 202, respectively. Reaction area 202, color calibration area 204, and temperature calibration area 206 may take on other shapes and arrangements.

Figure 3:
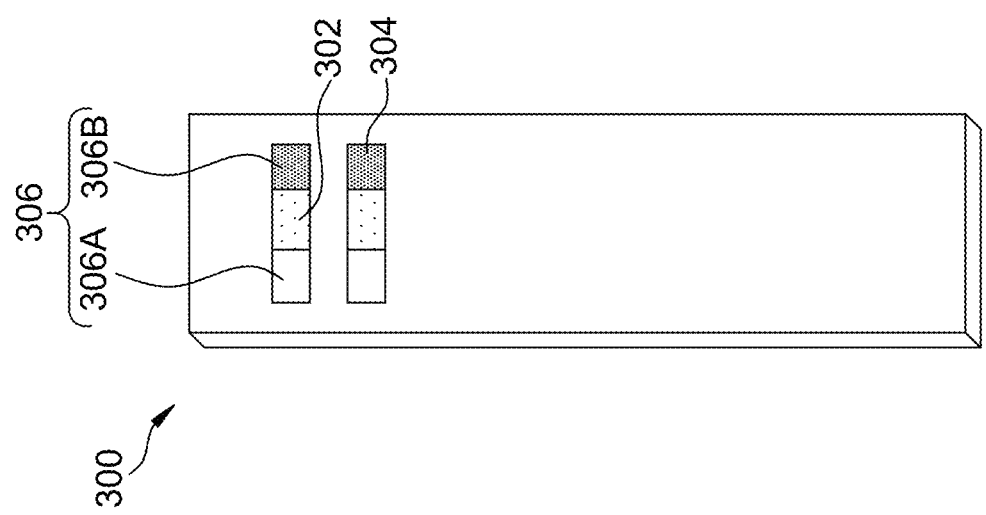
FIG. 3 shows a specimen test strip with a reaction area, a color calibration area, and a temperature calibration area in one or more examples of the present disclosure.

FIG. 3 shows a specimen test strip 300 with a different arrangement for a reaction area 302, a color calibration area 304, and a temperature calibration area 306 in one or more examples of the present disclosure. Color temperature area 306 is split into parts 306A and 306B, and reaction area 302 is sandwiched on the left and right sides by parts 306A and 306B, respectively. Color calibration area 304 is adjacent to the bottom side of the combination of reaction area 302 and temperature calibration area 306.

Figure 4:
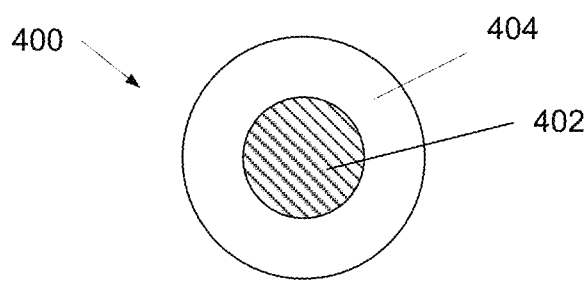
FIG. 4 shows an arrangement of a reaction area and a color calibration area in one or more examples of the present disclosure.

FIG. 4 shows an arrangement 400 of a reaction area 402 and a color calibration area 404 in one or more examples of the present disclosure. Color calibration area 404 surrounds reaction area 402. In one example, reaction area 402 has a circular shape and color calibration area 404 has a ring shape.

Figure 5:
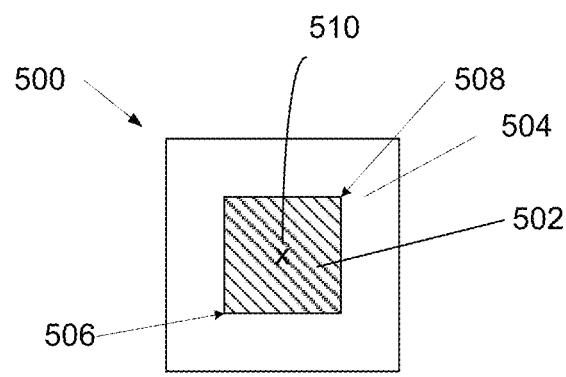
FIG. 5 shows an arrangement of a reaction area and a color calibration area in one or more examples of the present disclosure.

FIG. 5 shows an arrangement 500 of a reaction area 502 and a color calibration area 504 in one or more examples of the present disclosure. Like arrangement 400 (FIG. 4), color calibration area 504 surrounds reaction area 502. However, reaction area 502 has a rectangular shape and color calibration area 504 has a rectangular ring shape.

Figure 6:
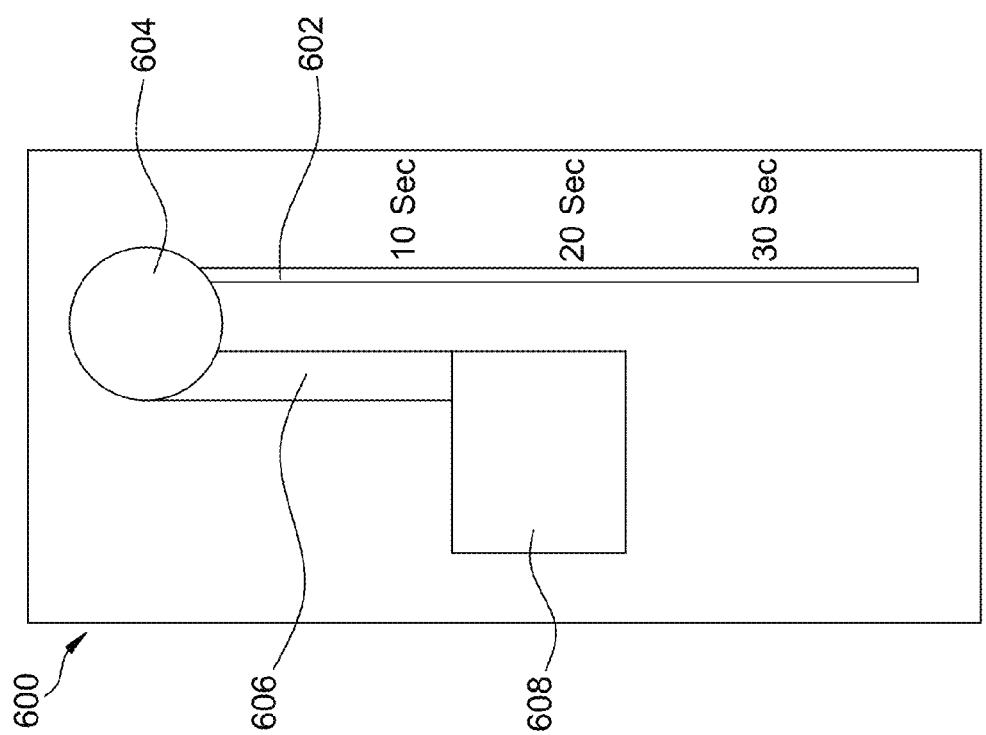
FIG. 6 shows part of a specimen test strip with a timer capillary in one or more examples of the present disclosure.

FIG. 6 shows part of a specimen test strip 600 with a timer capillary 602 in one or more examples of the present disclosure. Specimen test strip 600 represents a specimen test strip with any of the reaction area, color calibration, and temperature calibration arrangements described in the present disclosure. Specimen test strip 600 includes a capillary entrance 604, a reaction capillary 606, and a reaction area 608. Reaction capillary 606 connects capillary entrance 604 to reaction area 608. Timer capillary 602 is connected to capillary entrance 604. Timer capillary 602 has a smaller cross-section than reaction capillary 606. When a specimen sample is received at capillary entrance 604, reaction capillary 606 transports a majority of the specimen sample to reaction area 608 to detect the characteristic of the analyte. A small portion of the specimen sample travels along timer capillary 602, which is marked off with time durations so the progress of the specimen sample in timer capillary 602 is used as a timer to indicate when specimen test strip 600 should be read.

Figure 7:
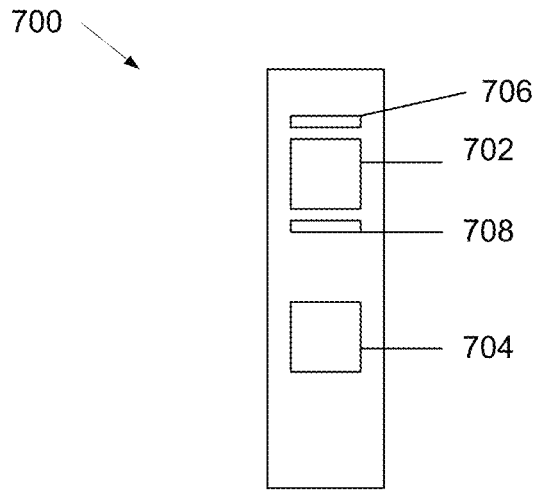
FIG. 7 shows a specimen test strip with a reaction area and a timer area in one or more embodiments of the present disclosure.

FIG. 7 shows a specimen test strip 700 with a reaction area 702 and a timer area 704 in one or more embodiments of the present disclosure. Specimen test strip 700 represents a specimen test strip with any of the reaction area, color calibration, and temperature calibration arrangements described in the present disclosure. Timer area 704 is another reaction area to receive the specimen sample. For example, like specimen test strip 600, specimen test strip 700 may include a reaction capillary that connects a capillary entrance and reaction area 702, and a timer capillary that connects the capillary entrance to timer area 704. Whereas reaction area 702 has reagents that produce a nonlinear reaction to the specimen sample, timer area 704 has reagents that produce a substantially linear reaction to the specimen sample so the color change of timer area 704 is used as a timer to indicate when specimen test strip 700 should be read. In one example, timer area 704 is hermetically sealed and includes cobalt chloride ($CoCl_2$) that changes from blue to pink in response to the water molecules in the specimen sample. Specimen test strip 700 may also include a color calibration area 706 and a temperature calibration area 708.

In one example, timer area 704 changes color in response to light once specimen test strip 700 is removed from an opaque sealed package. Timer area 704 changes color linearly in response to light to indicate an amount of time that specimen test strip 700 has been removed from its package, which may approximate a reaction time of reaction area 702 with a specimen sample to indicate when specimen test strip 700 should be read. Timer area 704 may be covered by a clear protective membrane. In one example, timer area 704 includes photochromic dyes such as azobenzens, salicylidene anilines, fulgides, spiropyrans, or spirooxazines.

In one example, timer area 704 changes color due to humidity once specimen test strip 700 is removed from a hermetically sealed package. Timer area 704 changes color linearly in response to humidity to indicate an amount of time since specimen test strip 700 has been removed from its package, which may approximate a reaction time of reaction area 702 with a specimen sample to indicate when specimen test strip 700 should be read. Timer area 704 may be covered by a perforated clear protective membrane that controls the exposure to humidity. In one example, timer area 704 includes $CoCl_2$ that changes from blue to pink.

Instead of using timer area 704, computing device 210 may use a built-in timer to approximate the reaction time of reaction area 702 with the specimen sample.

Figure 8:
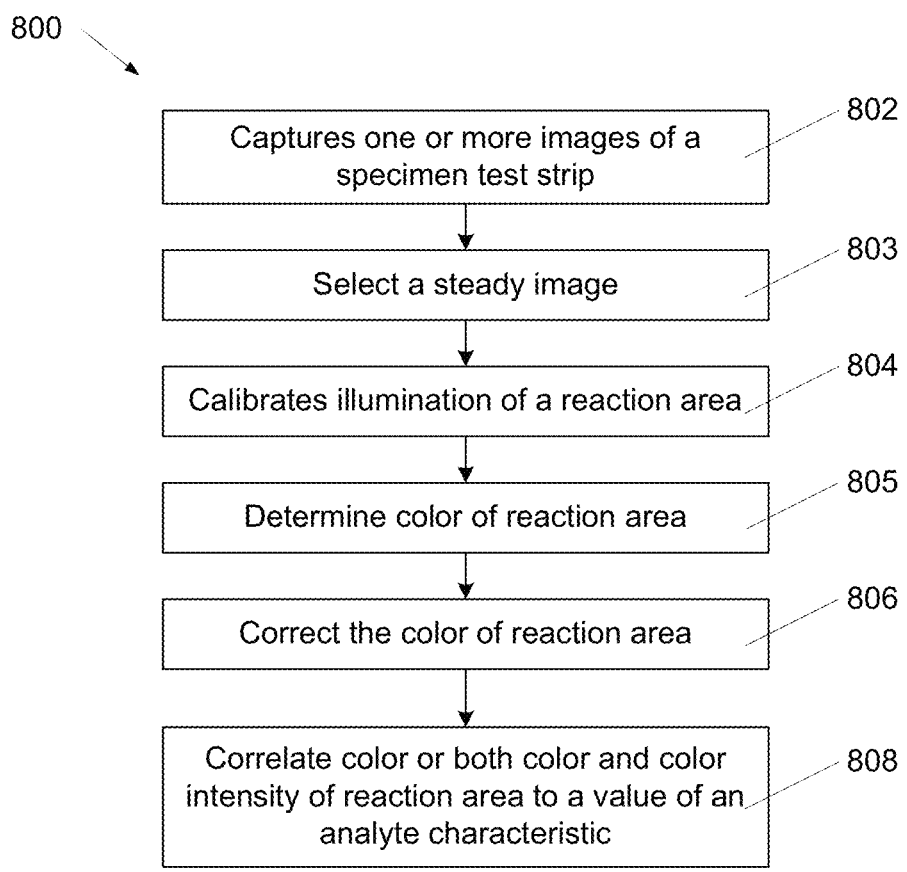
FIG. 8 is a flowchart of a method for a computing device executing a diagnostic application to calibrate and read a specimen test strip in one or more examples of the present disclosure.

FIG. 8 is a flowchart of a method 800 for a computing device (e.g., computing device 210 in FIG. 2) executing a diagnostic application to read a specimen test strip (e.g., specimen test strip 200 in FIG. 2) in one or more examples of the present disclosure. In any method described in the present disclosure, although the blocks are illustrated in a sequential order, these blocks may also be performed in parallel, and/or in a different order than those described herein. Also, the various blocks may be combined into fewer blocks, divided into additional blocks, and/or eliminated based upon the desired implementation. Method 800 may begin in block 802.

In block 802, computing device 210 captures one or more images 212 of specimen test strip 200. Multiple images 212 may captured so that a steady image without any blurring may be selected from images 212. Images 212 may be images taken in a rapid succession (e.g., in a continuous or rapid-fire mode) or frames from a video. In one example, each image 212 includes reaction area 202 and color calibration area 204. In another example, each image 212 also includes temperature calibration area 206. In yet another example, each image 212 further includes timer area 602 or 704.

When color calibration area 204 is a gray card, computing device 210 may use color calibration area 204 as an exposure reference for capturing images 212. Alternatively computing device 210 may use an object (e.g., grass or human skin) near specimen test strip that has about 18% reflectance as an exposure reference. Computing device 210 may automatically recognize the exposure reference or a user may direct imaging device 208 at the exposure reference to set the proper exposure.

In one example, computing device 210 captures images 212 at an appropriate time after the specimen sample is placed on specimen test strip 200. As previously described, timer area 602 or 704 may indicate when image 212 should be captured. Computing device 210 may monitor timer 602 or 704 and automatically capture image 212 or a user may direct imaging device 208 to capture image 212 from visually inspecting timer 602 or 704. Block 802 may be followed by optional block 803.

In optional block 803, computing device 210 selects a steady image 212 without any blurring. The diagnostic application may determine if an image 212 is steady by using a built-in accelerometer in computing device 210 to determining if computing device 210 was steady when it captured image 212. The diagnostic application may also use the built-in accelerometer to provide a warning when the user is not holding computing device 210 steady when an image 212 is about to be captured. Optional block 803 may be followed by block 804.

In block 804, computing device 210 calibrates the illumination of reaction area 202 in image 212. As previously described, computing device 210 estimates the illumination profile of reaction area 202 in image 212 and then corrects the illumination of reaction area 202 in image 212 when the illumination is not uniform. Block 804 may be followed by block 806.

In block 806, computing device 210 determines the color of reaction area 202 in image 212. As previously described, computing device 210 may determine the color of reaction area 202 based on color calibration area 204 in image 212 when area 204 is a color chart. Otherwise computing device 210 simply reads the color of reaction area 202 from image 212. Block 806 may be followed by block 807.

In block 807, computing device 210 corrects the color of reaction area 202 based on one or more calibration areas. In one example, computing device 210 corrects the color of reaction area 202 for white balance based on color calibration area 204 in image 212 when area 204 is a gray card. In one example, computing device 210 corrects the color of reaction area 202 for temperature based on temperature calibration area 206 in image 212. Note the order of blocks 806 and 807 may be reversed. Block 807 may be followed by block 808.

In block 808, computing device 210 correlates the color or both the color and the color intensity of sample pixels from reaction area 202 in image 212 to an analyte characteristic value (e.g., a glucose level).

Figure 9:
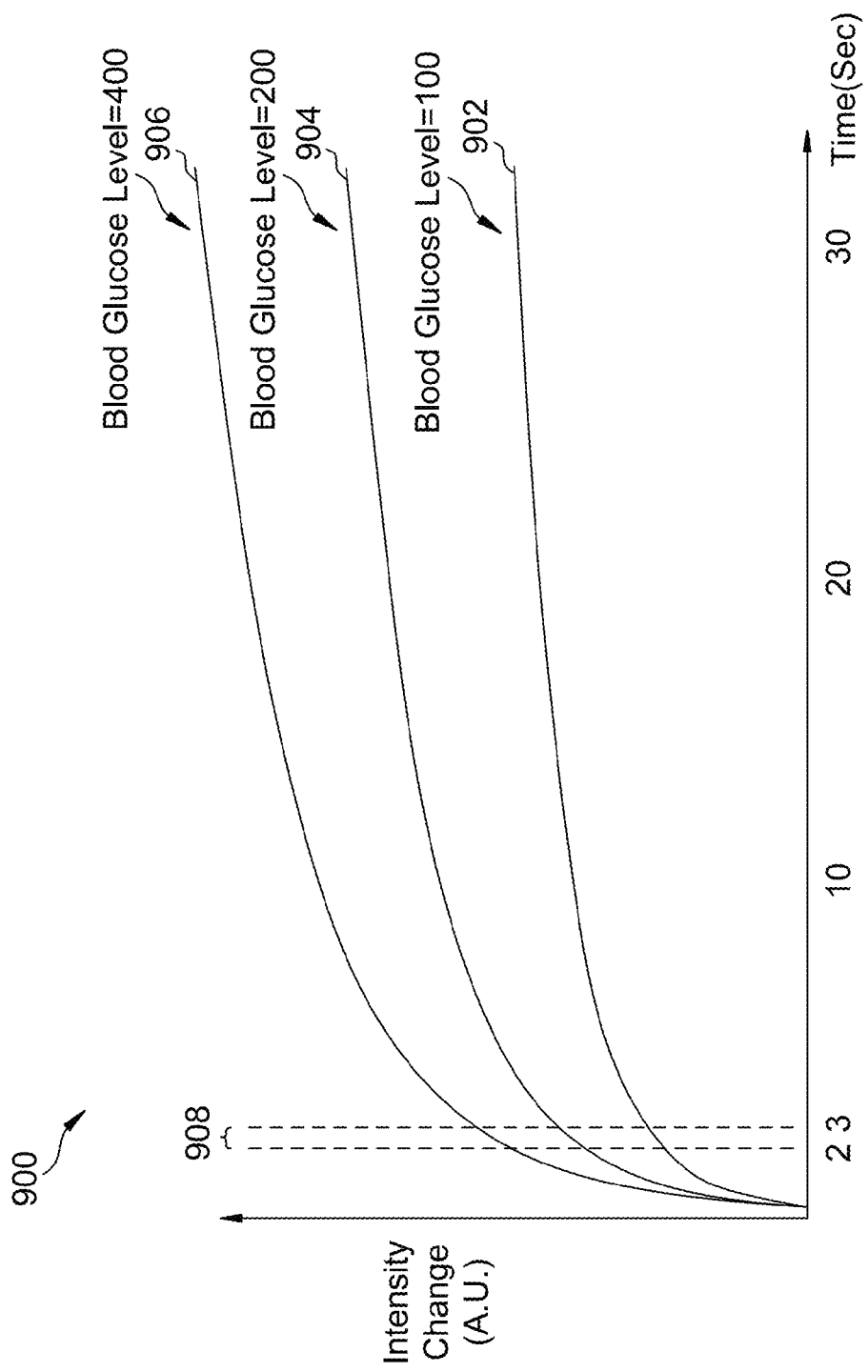
FIG. 9 is a chart illustrating curves plotting the change in a color parameter over time for values of an analyte characteristic in one or more examples of the present disclosure.

The rate of the change in a color parameter in reaction area 202 may depend on the analyte characteristic value. For each analyte characteristic value, the rate of the change in the color parameter may be plotted as a curve over time. FIG. 9 is a chart 900 illustrating three curves 902, 904, and 906 plotting the change in a color parameter (e.g., color intensity) over time for three analyte characteristic values (e.g., three glucose levels). Each curve has a different slope in a time window (e.g., time window 908) that is unique to the corresponding analyte characteristic value. Thus the difference between at least two values of the color parameter and the difference between when the two values are captured may be used to identify the corresponding analyte characteristic value. The time window is located earlier, such as at 2 and 3 seconds after the specimen sample is placed on specimen test strip 200, than the time one should wait to read a conventional specimen test strip, such as 10 seconds or more.

Figure 10:
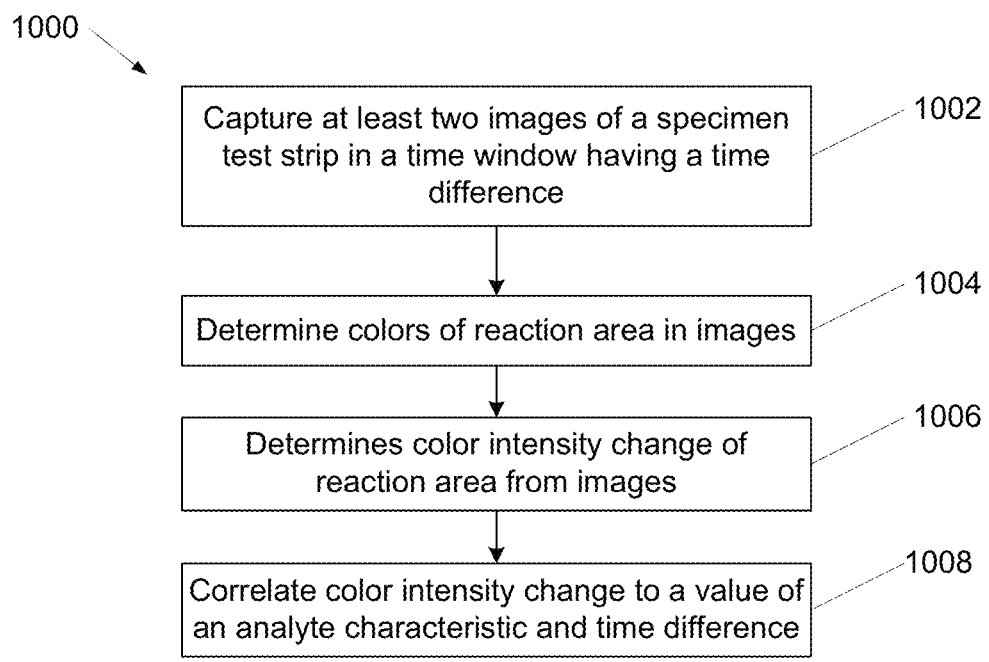
FIG. 10 is a flowchart of a method for a computing device executing a diagnostic application to use differential calculation to rapidly read a specimen test strip in one or more examples of the present disclosure.

FIG. 10 is a flowchart of a method 1000 for a computing device (e.g., computing device 210 in FIG. 2) executing a diagnostic application to use differential calculation to rapidly read a specimen test strip (e.g., specimen test strip 200 in FIG. 2) in one or more examples of the present disclosure. Method 1000 may begin in block 902.

In block 1002, computing device 210 captures at least two images 212 of specimen test strip 200 in time window 908. Images 212 may be images taken in a rapid succession (e.g., in a continuous or rapid-fire mode) or frames from a video. For example, a first image 212 is captured at a first time and a second image 212 is captured at a second time. The time difference between the first and the second time is calculated as a time window (e.g., time window 908 shown in FIG. 9). Each image 212 includes reaction area 202 on specimen test strip 200. In one example, each image 212 also includes color calibration area 204 on specimen test strip 200. In another example, each image further includes one or more additional calibration areas on specimen test strip 200, such as temperature calibration area 206. In one example, computing device 210 selects images 212 captured at time window 908 based on timer area 602 or 704. Block 1002 may be followed by a block 1004.

In block 1004, computing device 210 determines the color of reaction area 202 in each image 212 using any of the methods described in the present disclosure, including illumination correction, color correction, and temperature correction. Block 1004 may be followed by block 1006.

In block 1006, computing device 210 determines a change in color intensity of reaction area 202 from images 212. Block 1006 may be followed by block 1008.

In block 1008, computing device 210 correlates the change in color intensity to an analyte characteristic value. Computing device 210 may use chart 900, or the mathematical representation of chart 900, to determine the analyte characteristic value. Specifically, computing device 210 moves time window 908 along curves 902, 904, and 906. When the intensity change of a curve in the time window matches the intensity change of reaction area 202, then reaction area 202 has the analyte characteristic value of that curve.

Figure 11:
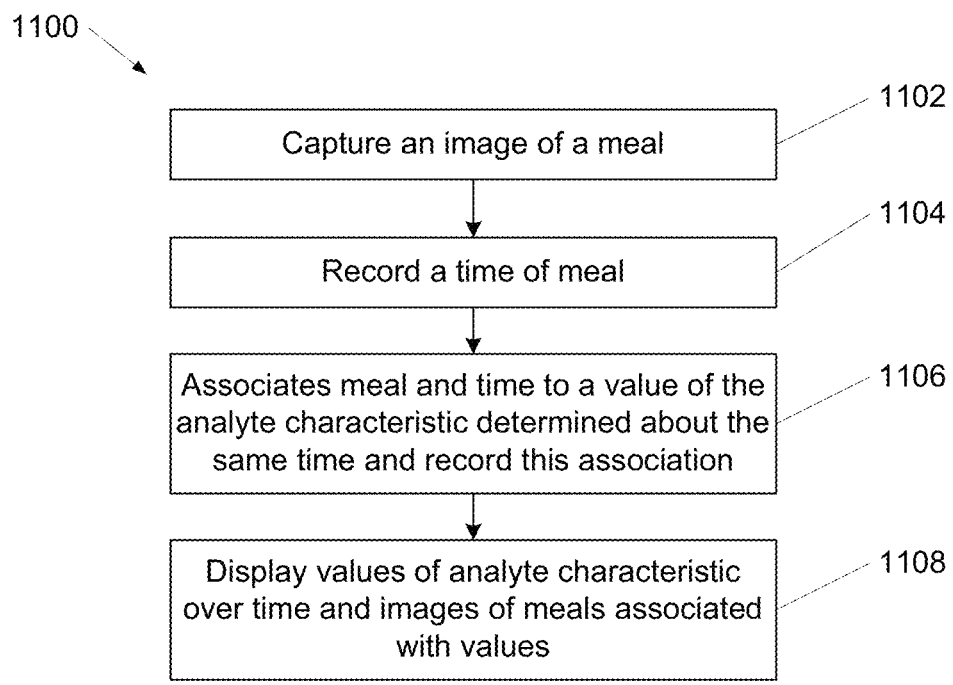
FIG. 11 is a flowchart of a method for a computing device executing a diagnostic application to track a user's diet along with an analyte characteristic in one or more examples of the present disclosure.

FIG. 11 is a flowchart of a method 1100 for a computing device (e.g., computing device 210 in FIG. 2) executing a diagnostic application to track a user's diet along with an analyte characteristic in one or more examples of the present disclosure. Method 1100 may begin in block 1102.

In block 1102, computing device 210 captures an image of a meal. Block 1102 may be followed by block 1104.

In block 1104, computing device 210 records a time of the meal. Block 1104 may be followed by block 1106.

In block 1106, computing device 210 associates the meal and the time to an analyte characteristic value determined about the same time and records this association. The analyte characteristic value may be determined using any of the methods described in the present disclosure. Blocks 1102, 1104, and 1106 may be repeated to track a user's diet over time. Block 1106 may be followed by block 1108.

Figure 12:
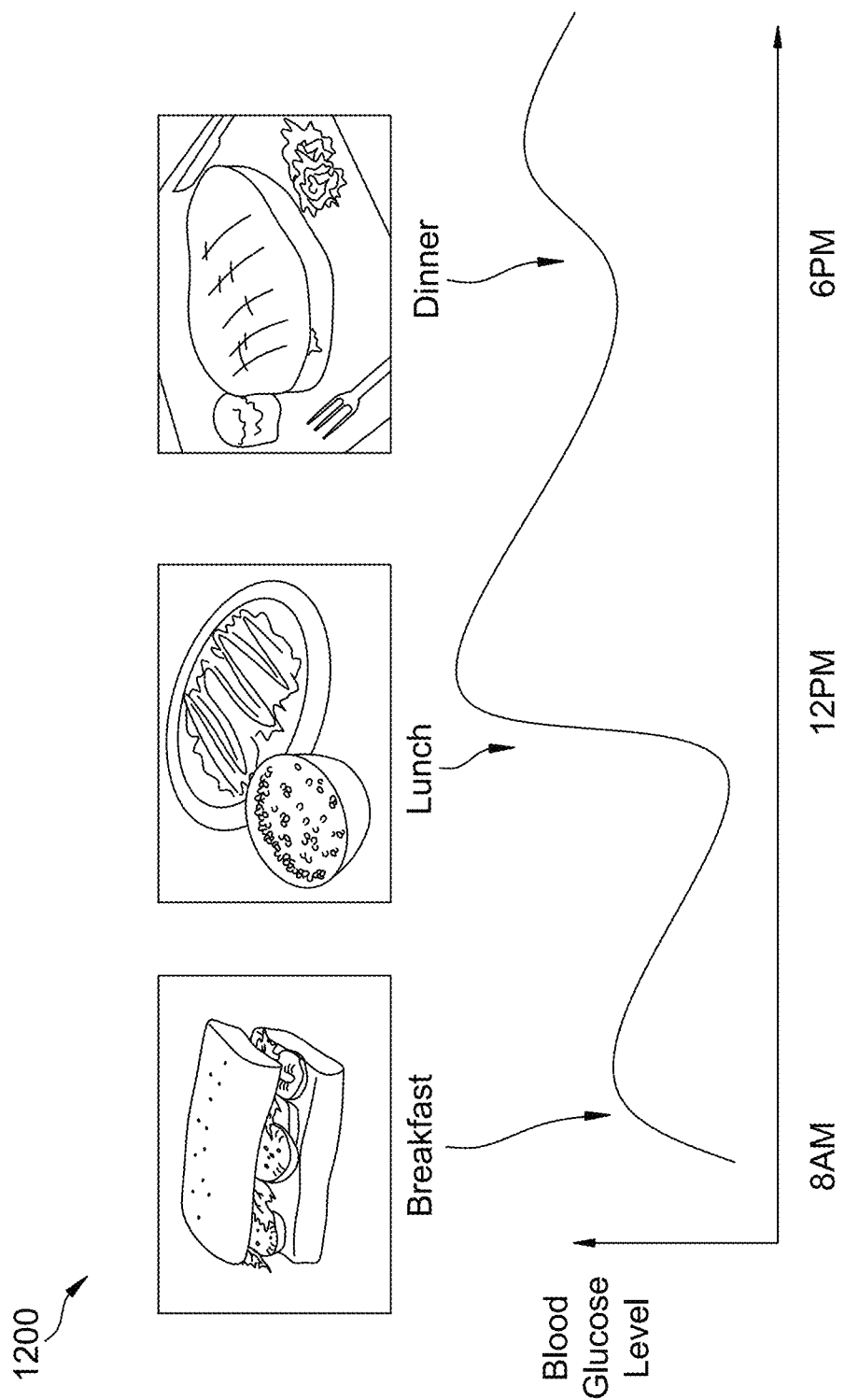
FIG. 12 graphically illustrates an association of meals, times, and analyte characteristic values over the course of a day in one or more examples of the present disclosure.

In block 1108, computing device 210 displays the recorded association. Computing device 210 may also transmit the recorded association over a computer network to another computing device, such as a doctor's computer, for treatment purposes. FIG. 12 graphically illustrates the association of meals, times, and analyte characteristic values over the course of a day in one or more examples of the present disclosure.

FIG. 13A shows a specimen test strip 1300 in one or more examples of the present disclosure. Specimen test strip 1300 includes a set of reaction areas 1302A, 1302B, 1302C, and 1302D (collectively as "reaction areas 1302" or individually as a generic "reaction area 1302"). Each reaction area 1302 is to detect a different range of values of an analyte characteristic in the specimen sample. In one example for detecting glucose level, reaction area 1302A detects 0 to 100 milligrams per deciliter (mg/dL), reaction area 1302B detects 0 to 200 mg/dL, reaction area 1302C detects 0 to 400 mg/dL, and reaction area 1302D detects 0 to 800 mg/dL. To detect different ranges of values of the analyte characteristic, reaction areas 1302 have different concentrations of one or more of the reagents. Alternatively reaction areas 1302 have different reagents.

Specimen test strip 1300 may include a capillary entrance and a capillary running through contacting reaction areas 1302 to deliver a specimen sample. Alternatively specimen test strip 1300 may include a spread zone that is overlapping and contacting reaction areas 1302 to distribute the sample to reaction areas 1302. The user may also manually spread the sample across reaction areas 1302 in an example without any structure to deliver the sample to reaction areas 1302. Specimen test strip 1300 may further include a color calibration area 1304 and a temperature calibration area 1306.

FIG. 13A shows specimen test strip 1300 in a pre-test condition. FIG. 13B shows specimen test strip 1300 receiving a 150 mg/dL glucose specimen sample in one or more examples of the present disclosure. As the concentration of glucose is higher than the range of reaction area 1302A, it has an oversaturated color so it is not used to determine the glucose level. However, reaction areas 1302B, 1302C, and 1302D may be used. The color of reaction area 1302B has a nice saturation so it may provide a better reading than reaction areas 1302C and 1302D.

FIG. 13C shows specimen test strip 1300 receiving a 300 mg/dL glucose specimen sample in one or more examples of the present disclosure. As the concentration of glucose is higher than the ranges of reaction areas 1302A and 1302B, they have oversaturated colors so they are not used to determine the glucose level. However, reaction areas 1302C and 1302D may be used. The color of reaction area 1302C has a nice saturation so it may provide a better reading than reaction area 1302D.

FIG. 13D shows specimen test strip 1300 receiving a 600 mg/dL glucose specimen sample in one or more examples of the present disclosure. As the concentration of glucose is higher than the ranges of reaction areas 1302A, 1302B, and 1302C, they have oversaturated colors so they are not used to determine the glucose level. The color of reaction area 1302D has a nice saturation so it is used to determine the glucose level.

In one example, reaction areas 1302 are rectangular and arranged in a single column to have an overall rectangular parameter. Reaction areas 1302 may take on other shapes and arrangements.

FIG. 14 shows a specimen test strip 1400 with a different arrangement for reaction areas 1402A, 1402B, 1402C, and 1402D (collectively "reaction areas 1402") in one or more examples of the present disclosure. In specimen test strip 1400, reaction areas 1402 are square and arranged to have a square outer parameter. Like specimen test strip 1300, specimen test strip 1400 may include structures to deliver a sample to reaction areas 1402 or the user may manually spread the sample across reaction areas 1402.

FIG. 15 shows a specimen test strip 1500 with a different arrangement for reaction areas 1502A, 1502B, 1502C, and 1502D (collectively "reaction areas 1502") in one or more examples of the present disclosure. In specimen test strip 1500, reaction subareas 1502 are triangular and arranged to have a square outer parameter. Like specimen test strip 1300, specimen test strip 1500 may include structures to deliver a sample to reaction areas 1502 or the user may manually spread the sample across reaction areas 1502.

FIG. 16 shows a specimen test strip 1600 with a different arrangement for reaction areas 1602A, 1602B, 1602C, and 1602D (collectively "reaction areas 1602") in one or more examples of the present disclosure. In specimen test strip 1600, a capillary entrance 1604 is connected by capillaries 1606 to reaction areas 1602. Reaction areas 1602 are equally spaced around capillary entrance 1604 at the same distance from capillary entrance 1604.

Figure 17:
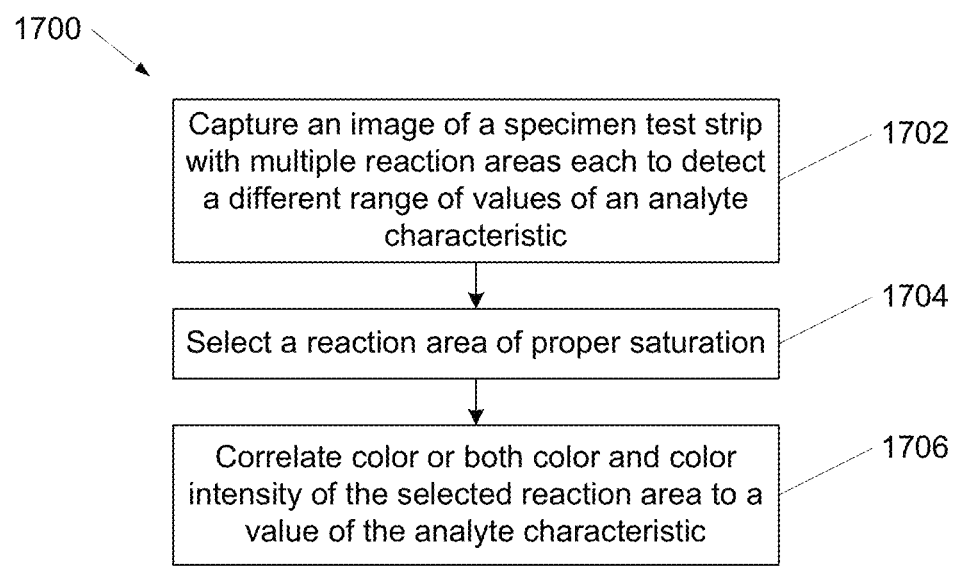
FIG. 17 is a flowchart of a method for a computing device executing a diagnostic application to read a specimen test strip with multiple reaction areas to detect different ranges of values of an analyte characteristic in one or more examples of the present disclosure.

FIG. 17 is a flowchart of a method 1700 for a computing device (e.g., computing device 210 in FIG. 2) executing a diagnostic application to read a specimen test strip (e.g., specimen test strip 1300 in FIG. 13) with multiple reaction areas to detect different ranges of values of an analyte characteristic in one or more examples of the present disclosure. Method 1700 may begin in block 1702.

In block 1702, computing device 210 captures an image of specimen test strip 1300. The image including reaction areas 1302. As previously described, each reaction area 1302 is to detect a different range of values of an analyte characteristic. Computing device 210 may determine the color of each reaction area 1302 using any of the methods described in the present disclosure. Block 1702 may be followed by block 1704.

In block 1704, computing device 210 selects a reaction area 1302 of the proper saturation. Computing device 210 examines reaction areas 1302 from the one with the smallest range to the one with the largest range. When the average RGB values of a reaction area 1302 are close to its noise level (e.g., ~10), which indicates that the analyte concentration has exceed its detection limit, computing device 210 proceeds to examine the next reaction area 1302. This process continues until computing device 210 selects a reaction area 1302 where the average RGB values are greater than its noise level. Block 1704 may be followed by block 1706.

In block 1706, computing device 210 correlates the color or the color and the color intensity of the selected reaction area 1302 to an analyte characteristic value.

Figure 18:
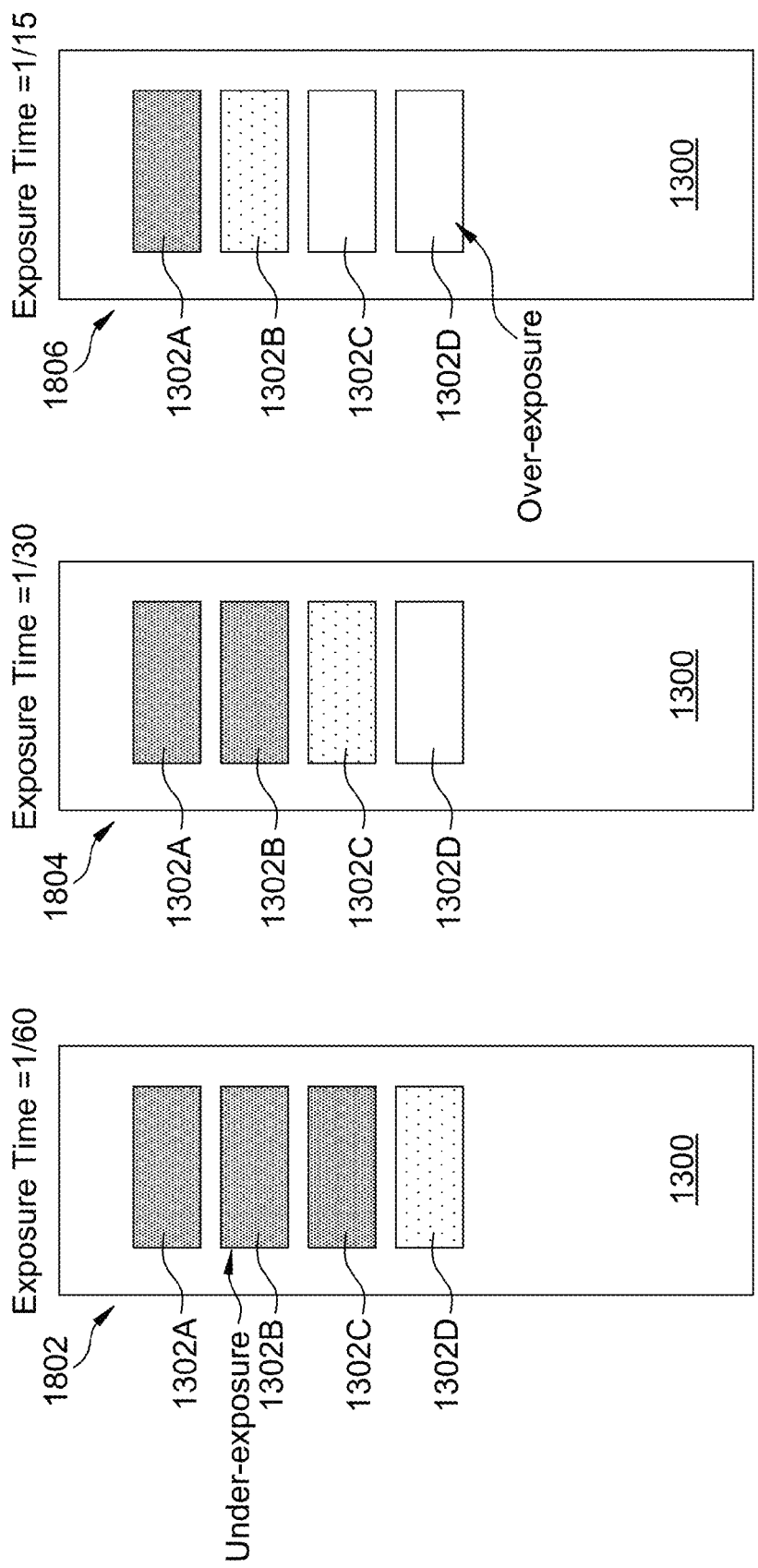
FIG. 18 shows a specimen test strip under different exposures to enhance the details of certain reaction areas in one or more examples of the present disclosure.

Method 1700 may be extended by taking multiple images of specimen test strip 1300 at multiple exposures in one or more examples of the present disclosure. FIG. 18 shows images 1802, 1804, and 1806 of specimen test strip 1300 at 1/60, 1/30, and 1/15 seconds, respectively, in one or more examples of the present disclosure. On one extreme, image 1802 is under-exposed to enhance the details of one or more reaction areas for detecting higher concentrations (e.g., reaction area 1302D), and thereby increasing the sensitivity of these reaction areas. On the other extreme, image 1806 is over-exposed to enhance the details of one or more reaction areas for detecting lower concentrations (e.g., reaction area 1302B), and thereby increasing the sensitivity of these reaction areas. With an exposure in between the extremes, image 1804 enhance the details of one or more reaction areas for detecting mid concentrations (e.g., reaction area 1302C), and thereby increasing the sensitivity of these reaction areas.

Computing device 210 may select one of images 1802, 1804, and 1806 based on the average RGB values of all of the reaction areas 1302 in each image. When the average RGB values of all of the reaction areas 1302 in an image is too low (e.g., <30) or too high (e.g., >240), which indicates the exposure time of this image to be improper, computing device 210 selects another image.

Figure 19:
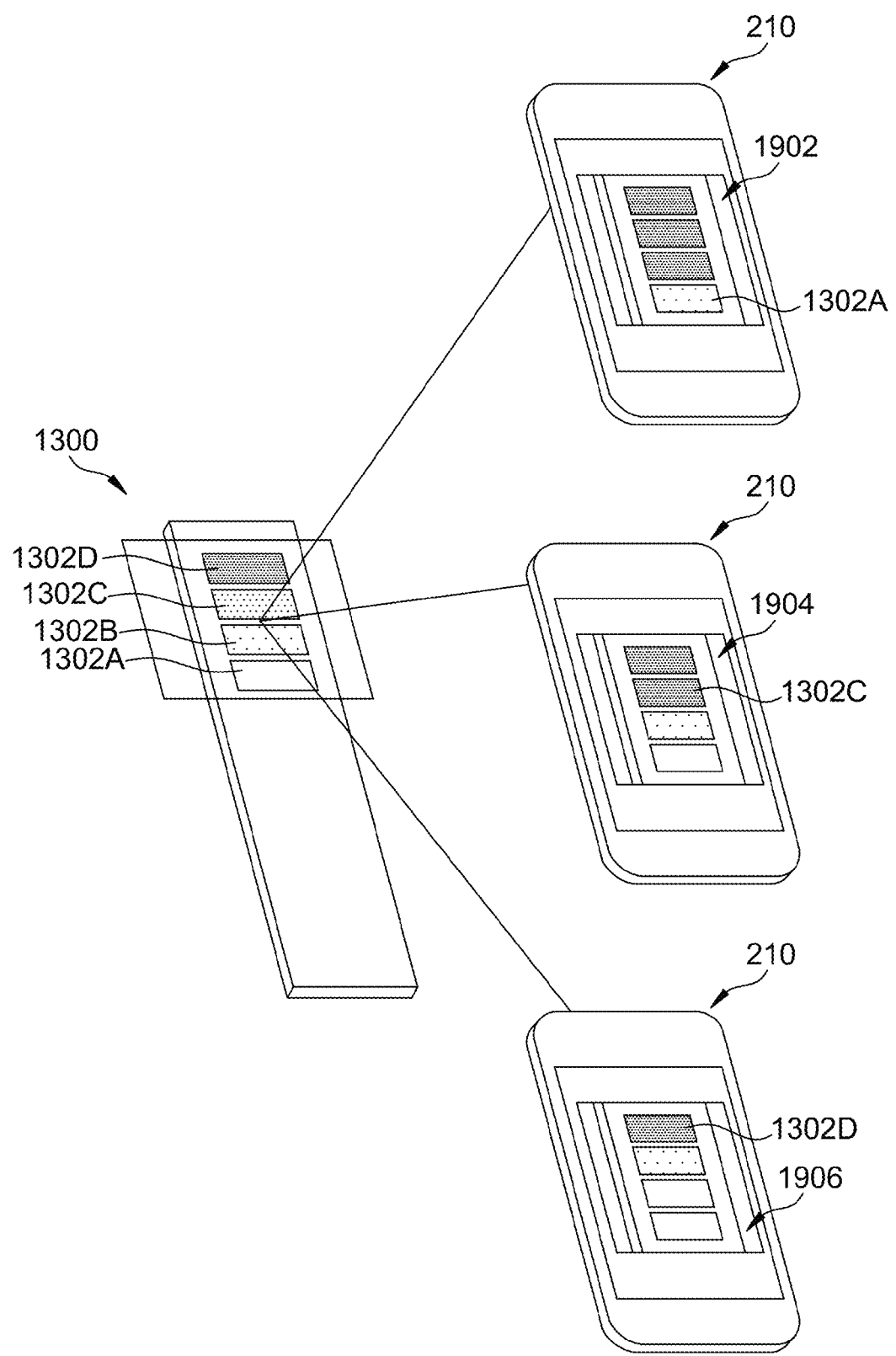
FIG. 19 shows a specimen test strip under different flash strengths to enhance the details of certain reaction areas in one or more examples of the present disclosure.

Instead of adjusting the exposure, method 1700 may be extended by taking multiple images of specimen test strip 1300 at multiple illumination strengths (e.g., flash or light strengths) in one or more examples of the present disclosure. FIG. 19 shows images 1902, 1904, and 1906 of specimen test strip 1300 at low, mid, and high flash strengths, respectively, in one or more examples of the present disclosure. On one extreme, image 1902 is under a low illumination strength to enhance the details of one or more reaction areas for detecting lower concentrations (e.g., reaction area 1302A), and thereby increasing the sensitivity of these reaction areas. On the other extreme, image 1906 is under a high illumination strength to enhance the details of one or more reaction areas for detecting higher concentrations (e.g., reaction area 1302D), and thereby increasing the sensitivity of these reaction areas. With a mid illumination strength, image 1904 enhance the details of one or more reaction areas for detecting mid concentrations (e.g., reaction area 1302C), and thereby increasing the sensitivity of these reaction areas.

In this mode, computing device 210 may test the illumination source (e.g., flash) prior to capturing images 1902, 1904, and 1906 to ensure it is working properly. For example, computing device 210 turns on the flash at least once and uses the detected intensity change to determine whether or not the flash is working.

Computing device 210 may select one of images 1902, 1904, and 1906 based on the average RGB values of the entire or part of reaction areas 1302 in each image. When the average RGB values of reaction areas 1302 in an image is either too low (e.g., <30) or too high (e.g., >240), which indicates the lighting intensity of this image to be improper, computing device 210 selects another image.

Figure 20:
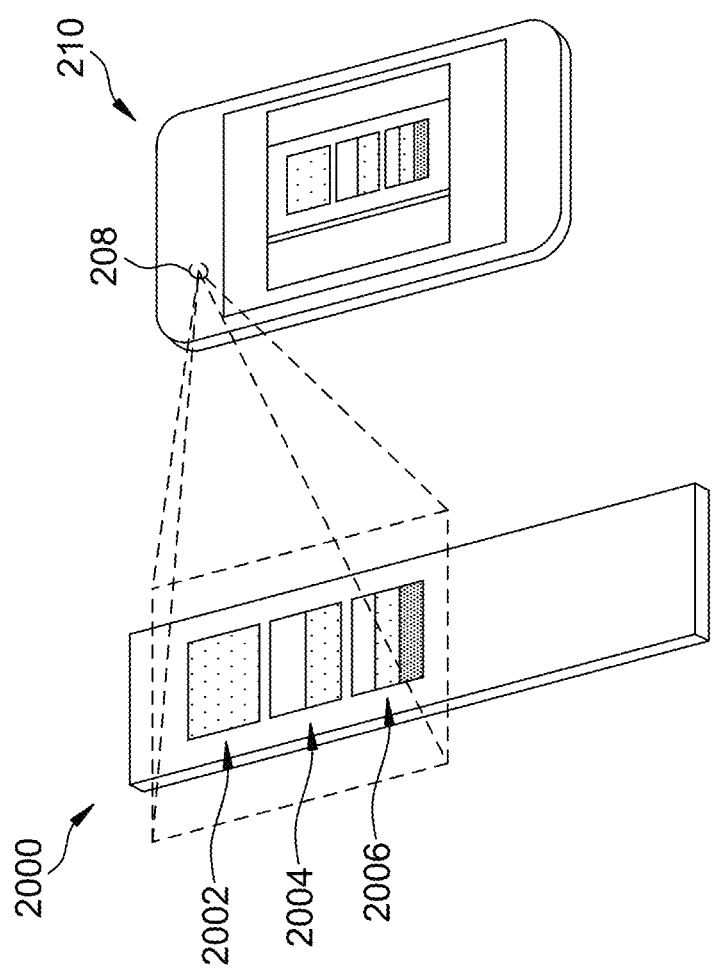
FIG. 20 shows a specimen test strip that includes multiple reaction areas to detect values of characteristics of different analytes in one or more examples of the present disclosure.

FIG. 20 shows a specimen test strip 2000 in one or more examples of the present disclosure. Specimen test strip 2000 includes multiple reaction areas to detect values of characteristics of different analytes. In one example, specimen test strip 2000 includes a reaction area 2002 for detecting a characteristic of a first analyte in a specimen sample, a reaction area or reaction areas 2004 (e.g., two reaction areas 2004) for detecting a characteristic of a second analyte in the specimen sample, and a reaction area or reaction areas 2006 (e.g., three reaction areas 2006) to detect a characteristic of a third analyte in the specimen sample. Like reaction areas 1302 described in FIG. 13A, multiple reaction areas 2004 each detect a different range of values of the characteristic of the second analyte, and multiple reaction areas 2006 each detect a different range of values of the characteristic of third analyte.

In one example, one analyte in the specimen sample is known to affect the detection of another analyte. For example, reaction area 2006 detects glucose in a blood sample and reaction area 2004 detects the level of hematocrit (HCT) in the blood sample. HCT level may be detected directly or indirectly (i.e., by determining the level of another substance in the blood sample). The diagnostic application determines the HCT level and then corrects the glucose level using a known relationship between the HCT and the glucose levels. This relationship may be determined experimentally, mathematically, or both. The diagnostic application may perform the HCT correction before or after any of the other corrections described in the present disclosure.

Figure 21:
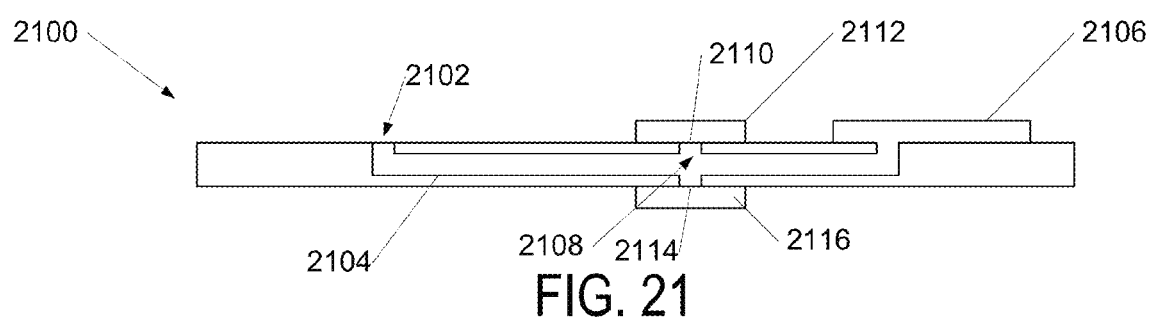
FIG. 21 is a cross-sectional view of a specimen test strip in one or more examples of the present disclosure.

Computing device 210 may also determine the HCT level in other ways from a specimen test strip. FIG. 21 is a cross-sectional view of a specimen test strip 2100 in one or more examples of the present disclosure. In specimen test strip 2100, a hole is provided in a path of the blood sample, a light is shone through the blood sample, and the resulting light color is correlated to the HCT level. In one example, specimen test strip 2100 includes a capillary entrance 2102, a capillary 2104 connected to capillary entrance 2102, and a reaction area 2106 connected to capillary 2104. A hole 2108 is defined through capillary 2104. A top opening 2110 of hole 2108 is covered by a transparent film 2112 and a bottom opening 2114 is covered by a transparent film 2116. Computing device 210 shines a light through hole 2108 and captures the color of the light exiting hole 2108, which depends on the percentage of red blood cells in the blood and is therefore correlated to the HCT level. In another example, film 2116 that is more reflective than film 2112. Part of the light is reflected or scattered back through top opening 2110 and captured by computing device 210 to determine the HCT level.

In another example, a rectangular strip of a material that filters red blood cells and absorbs serum is provided on a specimen test strip. The HCT level is then correlated to amount of serum absorbed, which is determined from the distance the blood sample travels up the strip.

Instead of using a timer area separate from a reaction area (e.g., timer area 602 or 704), method 800 may be extended by using a second color component of a reaction area to detect time and a first color component of the reaction area to detect an analyte characteristic in one or more examples of the present disclosure.

Figure 22:
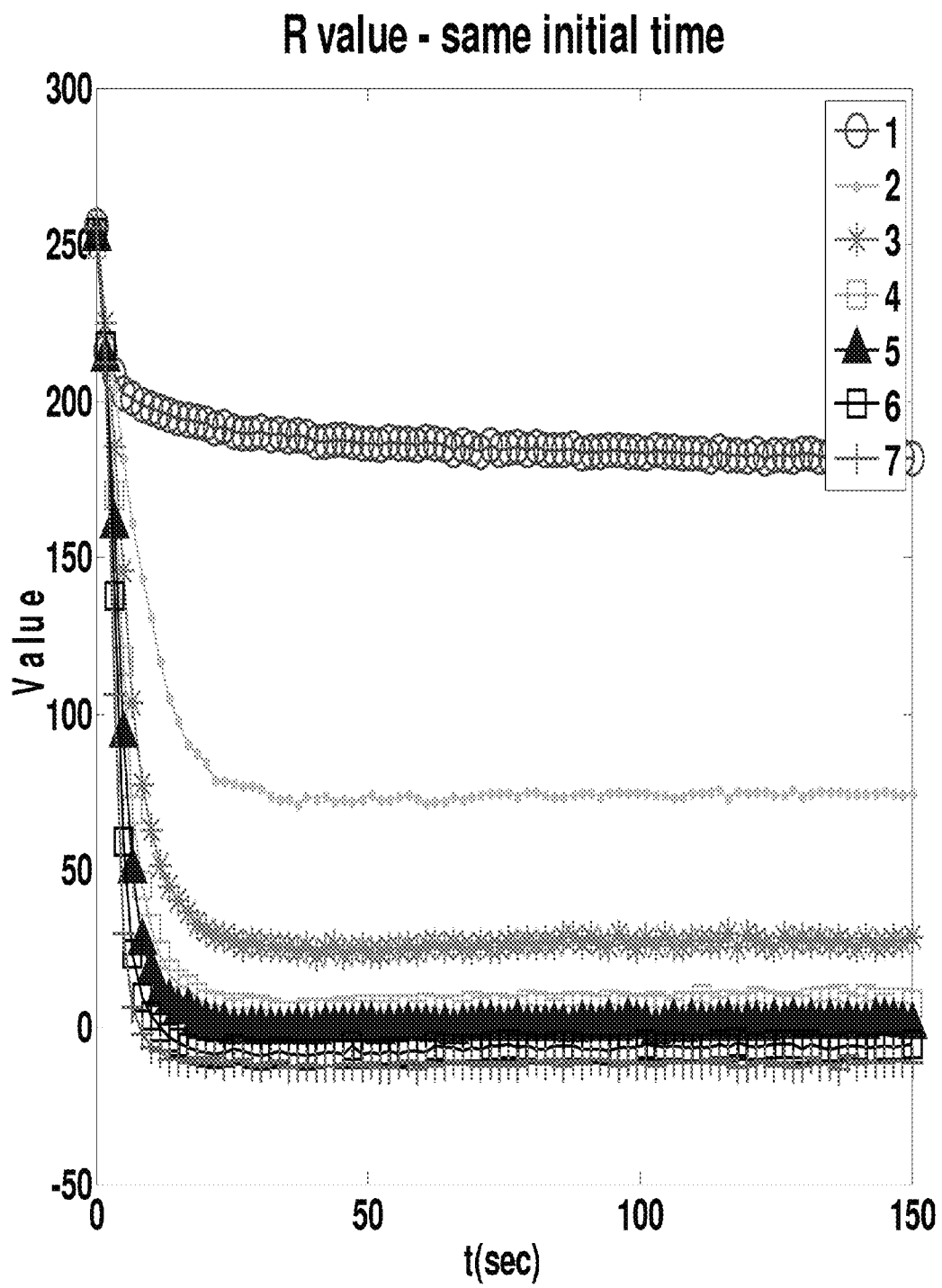
FIG. 22 is a chart illustrating curves plotting the change in a first color over time for values of a characteristic of a first analyte in one or more examples of the present disclosure.

FIG. 22 is a chart 2200 illustrating curves plotting the change in a first color component (e.g., red) of the reaction area over time for values of an analyte characteristic (e.g., glucose level in blood) in one or more examples of the present disclosure. As can be seen, the curves of the first color components quickly settle to constant values and therefore they may be used to indicate the respective values of the analyte characteristic.

Figure 23:
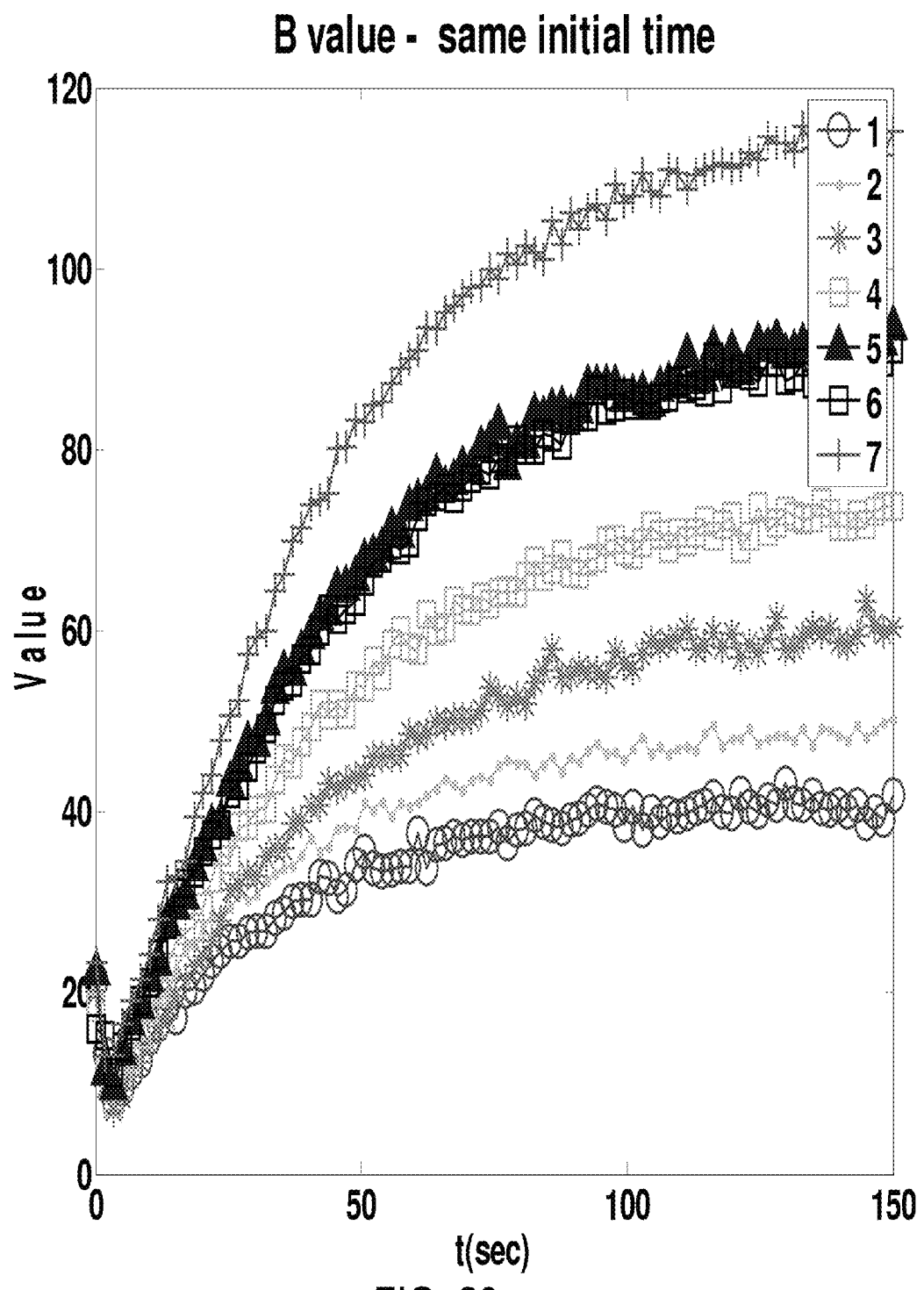
FIG. 23 is a chart illustrating curves plotting the change in a second color over time for values of a characteristic of a second analyte in one or more examples of the present disclosure.

FIG. 23 is a chart 2300 illustrating curves plotting the change in a second color component (e.g., a blue component) of the reaction area over time for values of the analyte characteristic in one or more examples of the present disclosure.

As can be seen, the curves of the second color component changes with time and therefore it may be used as a timer to indicate when to read the first color component and determine the value of the analyte characteristic (i.e., after the first color component settles). In one example, in block 802 of method 800, computing device 210 may capture multiple images 212, determine when the second color component indicates an appropriate time to read the first color component, and read the first color component at that time to determine a value of the analyte characteristic.

The test strips, systems and methods disclosed herein may be used to test for the presence and/or concentration of certain analytes, such as but not limited to glucose, cholesterol, uric acid, troponin I, ketone, protein, nitrite and leukocyte. Various fluids may be tested, such as but not limited to blood, interstitial fluid, urine, saliva, and other bodily fluids.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A specimen test strip to detect a characteristic of an analyte in a specimen sample, comprising:
    a reaction area to receive the specimen sample and change color based on the characteristic of the analyte in the specimen sample;
    a color calibration area comprising one or more samples with known color characteristics to be used to determine a color of the reaction area under different lighting conditions; and
    a temperature calibration area to change color based on its temperature to be used to adjust a measurement of the characteristic of the analyte.

2. The specimen test strip of claim 1, wherein the color calibration area is to be used to determine a color intensity in addition to the color of the reaction area after receiving the specimen sample.

3. The specimen test strip of claim 1, wherein the temperature calibration area comprises a plurality of temperature calibration parts.

4. The specimen test strip of claim 1, wherein the color calibration area surrounds the reaction area.

5. The specimen test strip of claim 4, wherein the color calibration area comprises a ring-shaped area.

6. The specimen test strip of claim 1, wherein the color calibration area comprises a dummy reaction area that comprises an enzyme in the reaction area but is devoid of a dye in the reaction area.

7. The specimen test strip of claim 1, wherein the color calibration area comprises a dummy reaction area that comprises a dye in the reaction area but is devoid of an enzyme in the reaction area.

8. The specimen test strip of claim 1, wherein the color calibration area comprises a color chart having known color samples or a gray card having a known reflectance.

9. The specimen test strip of claim 1, further comprising a timer capillary to receive the specimen sample, the timer capillary being marked off with time durations.

10. The specimen test strip of claim 1, further comprising a timer area to receive the specimen sample and to change color linearly in response to the specimen sample.

11. The specimen test strip of claim 1, further comprising a timer area to change color in response to light or humidity.

12. The specimen test strip of claim 1, further comprising an other reaction area to receive the specimen sample.

13. The specimen test strip of claim 12 wherein the reaction area detects glucose level and the other reaction area detects a hematocrit level.

14. The specimen test strip of claim 1, further comprising:
    a hole in a path of the specimen sample;
    a top opening of the hole being covered by a first film, the first film being transparent; and
    a bottom opening of the hole being covered by a second film.

15. The specimen test strip of claim 14, wherein the second film is more reflective than the first film.

* * * * *